(12) United States Patent
Neidert

(10) Patent No.: US 8,768,019 B2
(45) Date of Patent: Jul. 1, 2014

(54) DISPLAY OF AN ACQUIRED CINE LOOP FOR PROCEDURE NAVIGATION

(75) Inventor: Michael R. Neidert, Salthill (IE)

(73) Assignee: Medtronic, Inc., Minneapolis, MN (US)

( * ) Notice: Subject to any disclaimer, the term of this patent is extended or adjusted under 35 U.S.C. 154(b) by 620 days.

(21) Appl. No.: 13/020,543

(22) Filed: Feb. 3, 2011

(65) Prior Publication Data

US 2012/0201432 A1    Aug. 9, 2012

(51) Int. Cl.
*G06K 9/00* (2006.01)
*G06K 9/36* (2006.01)
*A61B 5/04* (2006.01)

(52) U.S. Cl.
USPC ........... 382/128; 382/103; 382/130; 382/131; 382/132; 382/287; 600/373; 600/374; 600/375; 600/424; 600/426

(58) Field of Classification Search
CPC ... G06T 7/0012; G06T 7/0024; G06T 7/0026; G06T 7/0028; G06T 7/0038; G06T 2207/30021; G06T 2207/30048; G06T 2207/30101; A61B 19/5244; A61B 2019/5265; A61B 2019/5289; A61B 2019/5297
USPC ............... 382/128, 103, 130, 131, 132, 287; 600/373, 374, 375, 424, 426
See application file for complete search history.

(56) References Cited

U.S. PATENT DOCUMENTS

| 7,386,339 | B2 * | 6/2008 | Strommer et al. | 600/424 |
| 7,945,304 | B2 * | 5/2011 | Feinberg | 600/411 |
| 2001/0031919 | A1 | 10/2001 | Strommer et al. | |
| 2003/0018251 | A1 | 1/2003 | Solomon | |
| 2004/0073105 | A1 * | 4/2004 | Hamilton et al. | 600/410 |
| 2004/0092815 | A1 | 5/2004 | Schweikard et al. | |
| 2005/0080336 | A1 * | 4/2005 | Byrd et al. | 600/428 |
| 2006/0058647 | A1 | 3/2006 | Strommer et al. | |
| 2007/0055142 | A1 * | 3/2007 | Webler | 600/425 |
| 2007/0149846 | A1 * | 6/2007 | Chen et al. | 600/117 |
| 2007/0167801 | A1 * | 7/2007 | Webler et al. | 600/459 |
| 2009/0198298 | A1 * | 8/2009 | Kaiser et al. | 607/17 |
| 2009/0226069 | A1 * | 9/2009 | Razzaque et al. | 382/131 |
| 2009/0234223 | A1 * | 9/2009 | Onoda et al. | 600/424 |
| 2010/0226537 | A1 * | 9/2010 | Villain et al. | 382/103 |
| 2011/0158488 | A1 * | 6/2011 | Cohen et al. | 382/128 |

OTHER PUBLICATIONS (PCT/US2012/020449) PCT Notification of Transmittal of the International Search Report and the Written opinion of the International Searching Authority, Mailed Apr. 18, 2012, 12 pages.

* cited by examiner

*Primary Examiner* — Michael A Newman
(74) *Attorney, Agent, or Firm* — Harness, Dickey

(57) ABSTRACT

The present disclosure relates to acquiring image data of a subject and selecting image data to be displayed. The image data can include a plurality of frames that relate to a specific location of a tracking device positioned within the subject. The determined location of the tracking device can be used to determine which frame of the image data to display at a selected time.

10 Claims, 4 Drawing Sheets

Image Correlation/Display Scheme
When DRF Tracked During Cine Loop Collection

Image Correlation/Display Scheme
When DRF Tracked During Cine Loop Collection

Predictive Image Display Scheme

DISPLAY OF AN ACQUIRED CINE LOOP FOR PROCEDURE NAVIGATION

FIELD

The present disclosure relates to acquisition of image data of a subject, and particularly to acquisition and display of image data based upon a physical location of a tracked portion of the subject.

BACKGROUND

This section provides background information related to the present disclosure which is not necessarily prior art.

Image data can be collected of a subject, such as a patient, at a selected rate and over a period of time. For example, a "cine loop" image data can include a plurality of frames that are collected at specific time points of the subject. Generally, the frames can be collected at a specific rate, such as about 10 to about 50 frames per second, to acquire a plurality of image data information of the subject. The plurality of frames can be displayed at a selected rate to illustrate motion of the subject over time, similar to a cinematic movie displaying a plurality of frames to represent motion or change in position of a particular object from one frame to the next.

During the procedure, such as a surgical procedure on a patient, the display of the image data on a display device can represent the structure of the subject. However, in various instances, structures within the subject may move over time. For example, a heart in the patient may move over time, such that a single static representation or illustration of the heart may not represent the actual position of the heart at a certain moment. Determining what frame of a plurality of collected frames, such as from the cine loop, to display to illustrate the exact location or configuration of the heart in a specific time point, can be troublesome.

SUMMARY

This section provides a general summary of the disclosure, and is not a comprehensive disclosure of its full scope or all of its features.

A structure of a subject, such as a heart or heart wall of a patient, can be illustrated over time based upon a determination of a position of the heart wall. For example, a tracking device, such as a reference tracking device, can be connected to a wall or a portion of the heart of the patient. The tracked location of the reference tracking device can be related to a frame in a cine loop image data of the heart. The cine loop image data can include a plurality of frames where each one relates to a tracked or determined location of the reference tracking device. Accordingly, subsequently tracking the reference tracking device can be used to determine which of the frames should be displayed on a display device to illustrate the current location or configuration of the heart. It will be understood that the reference tracking device can be connected to any appropriate structure, including a heart wall, diaphragm, abdomen wall, or the like and the location of the reference tracking device that relates to selected frames can be made. The correlation can be used to display the appropriate frame on a display device that relates to a later determined and tracked position of the reference tracking device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. As discussed herein, a cine loop can refer to a plurality of images acquired at a selected rate of any portion. The plurality of images can then be viewed in sequence at a selected rate to indicate motion or movement of the portion. The portion can be an anatomical portion, such as a heart, or a non-anatomical portion, such as a moving engine or other moving system.

Figure 1:
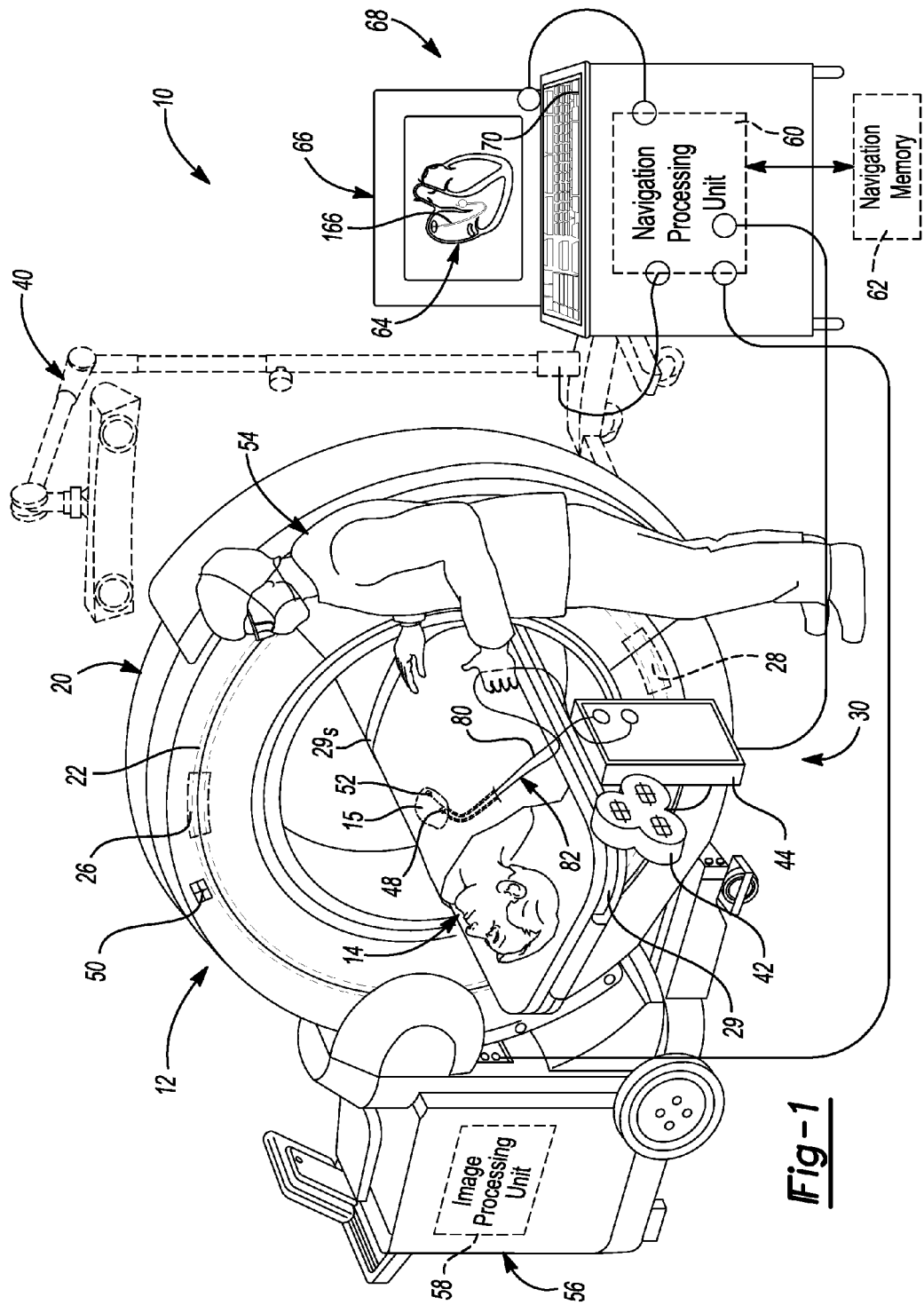
FIG. 1 is an environmental view of a subject with an imaging and navigation system.

FIG. 1 is a diagram illustrating an overview of a navigation system 10 that can be used for various procedures. The navigation system 10 can be used to track the location of an item, such as an implant or an instrument (e.g. instrument 80 as discussed herein), relative to a subject, such as a patient 14. It should further be noted that the navigation system 10 may be used to navigate any type of instrument, implant, or delivery system, including: guide wires, arthroscopic systems, ablation instruments, stent placement, orthopedic implants, spinal implants, deep brain stimulation (DBS) probes, etc. Non-human or surgical procedures may also use the instrument 80 and the navigation system 10. Moreover, the instruments may be used to navigate or map any region of the body. The navigation system 10 and the various tracked items may be used in any appropriate procedure, such as one that is generally minimally invasive or an open procedure.

The navigation system 10 can interface with or integrally include an imaging system 12 that is used to acquire pre-operative, intra-operative, or post-operative, or real-time image data of the patient 14. It will be understood, however, that any appropriate subject can be imaged and any appropriate procedure may be performed relative to the subject. The navigation system 10 can be used to track various tracking devices, as discussed herein, to determine locations of the patient 14. The tracked locations of the patient 14 can be used to determine or select images for display to be used with the navigation system 10. The initial discussion, however, is directed to the navigation system 10 and the exemplary imaging system 12.

In the example shown, the imaging system 12 comprises an O-Arm® imaging device sold by Medtronic Navigation, Inc.

having a place of business in Louisville, Colo., USA. The imaging device 12 includes imaging portions such as a generally annular gantry housing 20 that encloses an image capturing portion 22. The image capturing portion 22 may include an x-ray source or emission portion 26 and an x-ray receiving or image receiving portion 28. The emission portion 26 and the image receiving portion 28 are generally spaced about 180 degrees from each other and mounted on a rotor (not illustrated) relative to a track of the image capturing portion 22. The image capturing portion 22 can be operable to rotate 360 degrees during image acquisition. The image capturing portion 22 may rotate around a central point or axis, allowing image data of the patient 14 to be acquired from multiple directions or in multiple planes.

The imaging system 12 can include those disclosed in U.S. Pat. Nos. 7,188,998; 7,108,421; 7,106,825; 7,001,045; and 6,940,941; all of which are incorporated herein by reference. The imaging system 12 can also include or be associated with various image processing systems, as discussed herein. Other possible imaging systems can include C-arm fluoroscopic imaging systems which can also be used to generate three-dimensional views of the patient 14.

The patient 14 can be fixed onto an operating table 29, but is not required to be fixed to the table 29. The table 29 can include a plurality of straps 29s. The straps 29s can be secured around the patient 14 to fix the patient 14 relative to the table 29. Various apparatuses may be used to position the patient 14 in a static position on the operating table 29. Examples of such patient positioning devices are set forth in commonly assigned U.S. patent application Ser. No. 10/405,068, published as U.S. Pat. App. Pub. No. 2004-0199072 on Oct. 7, 2004, entitled "An Integrated Electromagnetic Navigation And Patient Positioning Device", filed Apr. 1, 2003 which is hereby incorporated by reference. Other known apparatuses may include a Mayfield® clamp.

The navigation system 10 includes a tracking system 30 that can be used to track instruments relative to the patient 14 or within a navigation space. The navigation system 10 can use image data from the imaging system 12 and information from the tracking system 30 to illustrate locations of the tracked instruments, as discussed herein. The tracking system 30 can include a plurality of types of tracking systems including an optical tracking system that includes an optical localizer 40 and/or an electromagnetic (EM) tracking system that can include an EM localizer 42 that communicates with or through an EM controller 44. The optical tracking system 40 and the EM tracking system with the EM localizer 42 can be used together to track multiple instruments or used together to redundantly track the same instrument. Various tracking devices, including those discussed further herein, can be tracked with the tracking system 30 and the information can be used by the navigation system 10 to allow for an output system to output, such as a display device to display, a position of an item. Briefly, tracking devices, can include a patient or reference tracking device (to track the patient 14) 48, an imaging device tracking device 50 (to track the imaging device 12), and an instrument tracking device 52 (to track the instrument 80), allow selected portions of the operating theater to be tracked relative to one another with the appropriate tracking system, including the optical localizer 40 and/or the EM localizer 42. The reference tracking device 48 can be positioned on an instrument 82 (e.g. a catheter) to be positioned within the patient 14, such as within a heart 15 of the patient 14.

It will be understood that any of the tracking devices 48-52 can be optical or EM tracking devices, or both, depending upon the tracking localizer used to track the respective tracking devices. It will be further understood that any appropriate tracking system can be used with the navigation system 10. Alternative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all herein incorporated by reference.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. Ser. No. 10/649,214, filed on Jan. 9, 2004, published as U.S. Pat. App. Pub. No. 2004/0116803, all of which are incorporated herein by reference.

With an EM tracking system, the localizer 42 and the various tracking devices can communicate through the EM controller 44. The EM controller 44 can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 40, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can further include a support housing or cart 56 that can house a separate image processing unit 58. The cart can be connected to the gantry 20. The navigation system 10 can include a navigation processing unit 60 that can communicate or include a navigation memory 62. The navigation processing unit 60 can include a processor (e.g. a computer processor) that executes instructions to determine locations of the tracking devices 48-52 based on signals from the tracking devices. The navigation processing unit 60 can receive information, including image data, from the imaging system 12 and tracking information from the tracking systems 30, including the respective tracking devices 48-52 and the localizers 40-42. Image data can be displayed as an image 64 on a display device 66 of a workstation or other computer system 68 (e.g. laptop, desktop, tablet computer which may have a central processor to act as the navigation processing unit 60 by executing instructions). The workstation 68 can include appropriate input devices, such as a keyboard 70. It will be understood that other appropriate input devices can be included, such as a mouse, a foot pedal or the like which can be used separately or in combination. Also, all of the disclosed processing units or systems can be a single processor (e.g. a single central processing chip) that can execute different instructions to perform different tasks.

The image processing unit 58 processes image data from the imaging system 12 and transmits it to the navigation processor 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design.

In various embodiments, the imaging system 12 can generate image data that can be registered to the patient space or navigation space. In various embodiments, the position of the patient 14 relative to the imaging system 12 can be determined by the navigation system 10 with the patient tracking device 48 and the imaging system tracking device 50 to assist in registration. Accordingly, the position of the patient 14 relative to the imaging system 12 can be determined.

Alternatively, or in addition to tracking the imaging system 12, the imaging system 12, such as the O-Arm® imaging system, can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference.

Subject or patient space and image space can be registered by identifying matching points or fiducial points in the patient space and related or identical points in the image space. When the position of the imaging device 12 is known, either through tracking or its "known" position (e.g. O-Arm® imaging device sold by Medtronic, Inc.), or both, the image data is generated at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 prior to the procedure for collection of automatically registered image data or cine loop image data. Also, the imaging system 12 can be used to acquire images for confirmation of a portion of the procedure.

Figure 2:
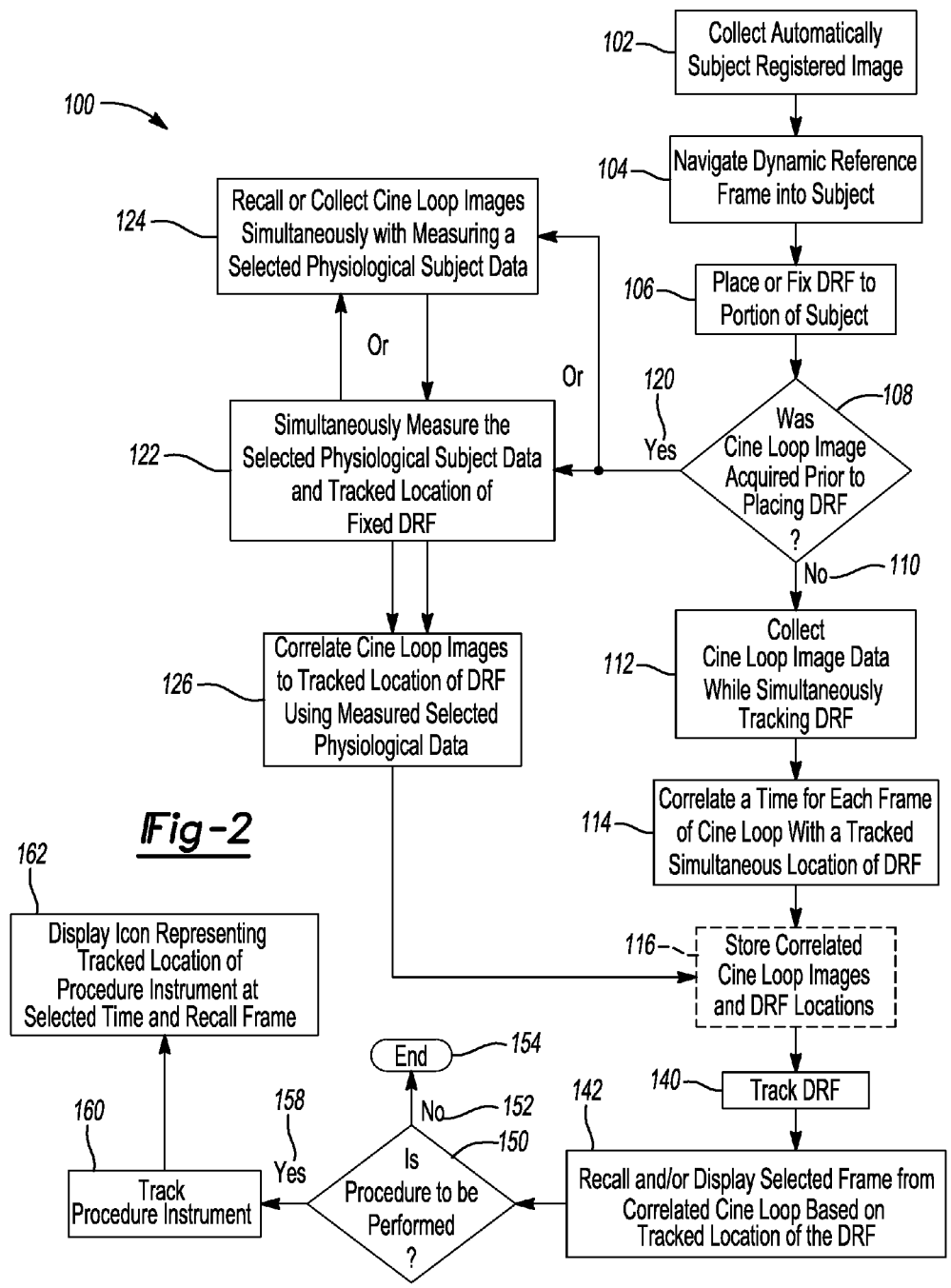
FIG. 2 is a flowchart of a method for collecting and displaying cine loop images.

With reference to FIG. 2, a system or flowchart 100 is illustrated to show a process or method of acquiring image data of a subject, such as the patient 14 and for subsequent illustration of the image data on the display 68 and navigation of a procedure with the instrument 80. It will be understood that the subject may also be any other imagable portion, such as a fuselage, non-human animal, etc. In the method 100, a plurality of images can be acquired of the patient 14, including the heart 15 of the patient 14, which can be displayed on the display 66 to illustrate a current location of the instrument 80 that is positioned within the heart 15 of the patient 14. It will be understood, however, that image data can be acquired of any portion of the patient 14, particularly a portion of the patient that moves over time. For example, a portion of the patient 14 can include lungs, diaphragm, or other circulatory systems that may move over time. The image data can be acquired of the patient 14 and can be registered to the patient to allow for a cinematic "cine loop" illustration of the patient or portion of the patient when the instrument 100 is positioned within the patient 14, such as within the heart 15. The cine loop can include a plurality of images collected in succession and operable to be displayed in succession to illustrate a representation of motion and/or change in configuration of a structure, such as the heart 15.

With continuing reference to FIG. 2, and additional reference to FIG. 1, the method 100 can begin by collecting automatically registered images in block 102. The automatically registered images can be acquired with the imaging system 12, illustrated in FIG. 1. As discussed above, the imaging system 12 can collect images of the patient 14, including the heart 15, that are registered to the position of the patient 14. Various methods and mechanisms, as discussed above, can be used to automatically register the images acquired with the imaging system 12 relative to the patient 14. In one example, the position of the patient 14 and the imaging device 12 can be known during image acquisition.

The images collected and automatically registered in block 102 allow intraoperative image data acquisition of the patient 14 for positioning various portions or items within the patient 14. For example, a dynamic reference frame, such as the dynamic reference frame 48 discussed above, can be navigated into the subject in block 104. The navigation of the internal dynamic reference frame 48 into the patient 14 can be done under fluoroscope guidance, such as with the imaging system 12. Alternatively, it can be understood that the internal dynamic reference frame 48 can be positioned in the patient 14 using any generally known technique, and can be tracked using the tracking system 30. The DRF 48 can be fixed or placed a portion of the patient in block 106. The internal DRF 48 can be fixed to the patient 14 in any appropriate location, such as affixing the internal DRF 48 to the right ventricular in the heart, such as the right ventricle apex, or the coronary sinus. The internal DRF 48 can be positioned in any appropriate location within the heart 15 and a location or internal DRF 48 can then be used to track and dynamically determine motion of the heart 15 within the patient 14. Also, the internal DRF 48 can be fixed to a structure or well of the heart 15, such as with a helix screw.

As is understood, the internal DRF 48 can be tracked with the tracking system 30 which may be the EM tracking system. Accordingly, a movement of the internal DRF 48 can be determined over time as the heart beats at its normal rhythm, or a rhythm imposed upon the heart 15 during the operative procedure. As will be discussed in greater detail herein, the internal DRF 48 can move to different three dimensional positions within the heart 15 as the heart 15 moves during time. Accordingly, as the heart 15 beats over time, the internal DRF 48 can move to a plurality of three dimension locations. However, the beating of the heart 15 is generally cyclic and the internal DRF 48 will generally move within a cycle, such as within a limited range of motion within the heart 15. Also, due to the cyclic nature, the DRF 48 will pass through the same positions over time as the heart 15 beats. For example, when the heart 15 is contracted, the DRF 48 will generally be at the same location during each contraction. Nevertheless, the movement of the heart or a portion of the heart to which internal DRF 48 is attached can be continuously tracked with the tracking system 30 using the internal DRF 48 that is fixed or replaced in the heart 15.

Once the internal DRF 48 is positioned within the patient 14 in block 106, a determination block can determine whether cine loop image data was acquired prior to placing the DRF in block 108. Although two possibilities can occur from the decision block 108, initially the following discussion will be directed to following a NO path 110 to a collection of cine loop image data while simultaneously tracking locations of the placed DRF 48 in block 112.

Collecting the cine loop image data while simultaneously tracking the DRF 48 includes imaging the patient 14 over time and tracking location of the DRF 48 placed in the patient 14 in block 106 over the same time period. According to various embodiments, an imaging system, such as the imaging system 12 that can include the O-Arm® imaging system or other fluoroscopic imaging systems, can acquire image data of the patient 14, including the heart 15, over a specified time period. During the specified time period a selected frame rate of images can be acquired of the patient 14, for example, about 30 frames (e.g. image frames) per second can be captured. It will be understood, however, that any appropriate frame rate, such as 10 frames per second, 20 frames per second, or 60 frames per second, can be collected. Regardless of the frame rate, the frames can be displayed in sequence to illustrate a motion of the patient 14, such as the heart 15, over time. Similar to a cinematic movie where a plurality of frames are shown in a selected sequence and speed to achieve an illusion of motion on a display. Accordingly, the plurality of frames collected can be displayed on a display device, such as the display device 66 to illustrate motion of the heart 15 over time in a "cine loop". The time period can be any appropriate time period and each frame can be collected at a time point $t_x$. For example a time period can be from time point $t_1$ to $t_n$, where each frame is collected at each time point $t_x$ in the time point $t_1$ and $t_n$.

During the acquisition of the image data in block 112, the DRF 48 positioned in the patient 14 can be tracked over the same time period. Additionally, the location of the DRF 48 can be tracked at a similar rate or at a faster rate or at a slower rate relative to the acquisition of the image data. Nevertheless, it can be selected to track or determine the location of the DRF 48 during or for each of the frames at time points $t_1$ to $t_n$. Accordingly, a location of the DRF 48 for each of the frames collected in the image data can be correlated to a tracked location of the DRF 48. The DRF 48 can be tracked in any appropriate degrees of freedom of movement including an x, y, z three dimensional position and selected orientation positions, if selected.

Once the image data is collected while simultaneously tracking and the DRF 48 in block 112, a correlation can be made between the multiple frames collected of the image data and the tracked locations of the DRF 48 in block 114. As discussed above, it can be selected to correlate each of the frames of the image data acquired to a tracked location of the DRF 48. The following discussion relates to correlation of images to tracked locations of the DRF 48. It will be understood, that alternatively, a procedure can be navigated with images that are correlated using various techniques including gating frame selection techniques as disclosed in U.S. patent applications Ser. No. 12/183,688, filed on Jul. 31, 2008, and published as U.S. Pat. App. Pub. No. 2010/0030061, published on Feb. 4, 2010, incorporated herein by reference.

Figure 3:
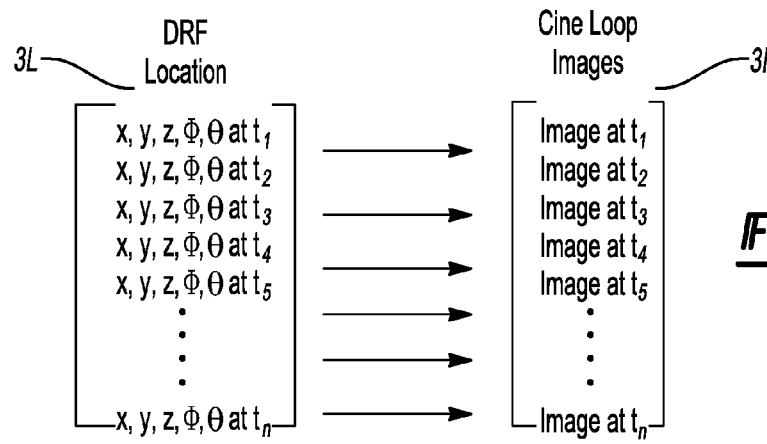
FIG. 3 is a diagram illustrating a correlation between a reference tracking device and cine loop images.

As illustrated in FIG. 3, in the left column 31 the location of the DRF 48 can be tracked for the period and at each of the time points $t_1$ through $t_n$. Each of these DRF 48 locations can be correlated to a cine loop image or frame, as discussed above. The plurality of images can be placed in a cine loop to illustrate motion of the heart 15. As illustrated in FIG. 3, in the left hand column 31 each of the tracked locations at each of the time points relate to an image or frame in the cine loop at each of the time points $t_1$ through $t_n$, as illustrated by the arrows 3a.

The correlation can be done during the tracking of the DRF 48 and the acquisition of the images or after the acquisition of the images and the tracked location of the DRF 48. For example, every time an image is acquired, the location of the DRF 48 can be tracked or determined and correlated substantially simultaneously. Alternatively, the DRF 48 can be tracked by a lead tracking system 30 and the cine loop images can be acquired by the imaging system 12. The specific times for each of the images at time points $t_1$ through $t_n$ can be saved with each of the images any the specific times of the tracked location of the DRF 48 at time $t_1$ though $t_n$ can be saved by the tracking system 30. An appropriate system, such as the navigation system 10 including the processor system 68, can then correlate the two specific times for a tracked location of the DRF 48 and an image in the cine loop acquired by the image system 12. In other words, as a high level example, if an image is acquired at 1100 hours and 5 seconds, and a tracked location of the DRF 48 is acquired at 1100 hours and 5 seconds, the frame and the tracked location of the DRF 48 can be correlated. It will be understood, the system, such as the processor system 68 can execute instructions to perform the correlation based on the time points of the acquisition of the cine loop image data (e.g. frames) and the determined locations of the DRF 48 at the same time points. Generally, each frame will have at least one DRF 48 location that is correlated with that frame. Thus, the location of he DRF 48 can be used to select or determine which correlated frame illustrates the configuration and/or location of the heart 15. In other words, at a later time when the DRF 48 is determined to be at a location that location can be used to select which of the frames, based on the correlated DRF 48 location, should be illustrated.

It will also be understood, however, that the acquisition of the image data by the imaging device 12 and the tracked location of the DRF 48 can be coordinated and correlated with the navigation system 10. For example, the beginning of the tracking and the beginning of the image acquisition may happen at a time 0 and each time a frame of the cine loop is collected by the imaging system 12, a tracked location of the DRF 48 can be saved. Thus, the imaging and tracked location determination can happen simultaneously and be coordinated as such. They can then be correlated within the navigation system 10.

After the correlation of the image data to the tracked location of the DRF 48, as illustrated in FIG. 3 occurs in block 114, the correlated cine loop images and DRF tracked locations can be stored in block 116. The stored correlated images and tracked locations can be stored within the memory system of the navigation memory 62 or as a part of the image processing unit 58. Nevertheless, the images can be stored in a selected memory, such as a substantially permanent memory or flash memory, for display and/or recall at a selected time. The stored images can be correlated to the tracked locations of the DRF 48 such as with a look-up table or index.

As discussed further herein, various frames of the cine loop can be displayed based upon a tracked location of the DRF 48. However, it will be understood that the decision block 108 on whether the cine loop image data was acquired prior to placing the DRF 48 can follow a YES path 120. Accordingly, prior to continuing discussion of performing a procedure with image data correlated with the DRF 48 location, a discussion of acquiring image data prior to placing the DRF 48 in block 106 will be discussed by following the YES path 120 from the decision block 106 of whether the cine loop image data was acquired prior to placing the DRF 48.

After a determination of following the YES path 120, due to the determination that the cine loop image data was acquired prior to placing the DRF 48 in block 108, one of two possibilities can occur. One possibility is that a simultaneous measurement of selected physiological subject data and a tracked location of the DRF can occur in block 122. Alternatively, a path can be followed to recall or collect cine loop images simultaneously while measuring the selected physiological data of the subject in block 124. The reason that either path to block 122 or 124 can be followed after the determination of the YES path 120 will be clear after the following discussion. Regardless, tracked and determined locations of the DRF 48 that is placed in block 106 can be correlated to a physiological measurement of the subject and/or can be correlated to image data that is acquired of the subject. Accordingly, the processes in blocks 122 or 124 may happen in any selected order and one need not occur before the other.

For the following discussion, simultaneously measuring the subject data and tracking location of the DRF 48 in block 122 will be selected to occur first. Generally, the DRF 48 is paced in the subject, such as the patient 14 in block 106. A selected physiological measurement of the patient 14 can then be made after the DRF 48 is positioned in the patient 14. The physiological measurement of the patient can be any appropriate measurement, such as a respiration, heart rhythm measurement, various polarizations or depolarization's within the heart, or any selected physiological measurements. Generally, a physiological measurement can include measurements of the patient 14 that relate to the physiology of the patient 14 based on the patient's 14 anatomy. For example, an electro-cardiogram (EKG) can be made of the patient 14 that relates to a rhythm of the heart 15 of the patient 14. The measurement of the heart 15 with an EKG can be made while tracking the location of the DRF 48. A correlation between the tracked location of the DRF 48 and various peaks (e.g. amplitudes) and valleys (e.g. amplitudes) in EKG can then be made or saved. Accordingly, the location of the DRF 48 as it relates to any particular portion of the measured EKG can be determined.

Cine loop frames image can be acquired of the patient 14 using any appropriate imaging system, such as a magnetic resonance imaging (MRI) or computed tomography (CT) imaging devices. Thus, cine loop or any plurality of images need not be acquired with the DRF in the portion of the subject being imaged. According to various embodiments, the DRF can be placed and an image system, such as the O-Arm® imaging system, can image the subject with the DRF in place, but the DRF is not required to be in place while imaging occurs, according to various embodiments. In various embodiments, the DRF 48 can not (e.g. magnetic coils in a magnet of a MRI) or can be selected to not be positioned in the patient 14 during the acquisition of the cine loop frames. As discussed above, the cine loop data can include the acquisition of a plurality of image frames of the patient 14 over a selected period of time such as between time points $t_1$ through $t_n$. During the acquisition of the cine loop frames in block 124, physiological measurement of the patient 14 can also be collected.

Figure 4:
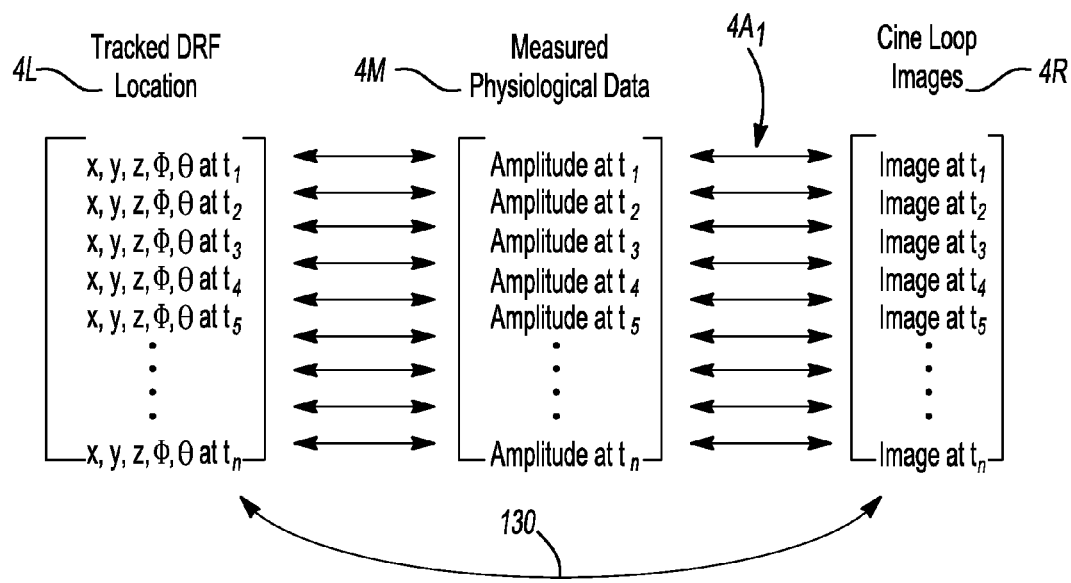
FIG. 4 is a diagram illustrating a correlation between a tracked location reference tracking device, a physiological measurement, and a frame cine loop image.

In one example, as illustrated in FIG. 4, the cine loop can be acquired while measuring an EKG of the patient 14. The physiological measurement, or a selected portion thereof, can be correlated to each image in the cine loop frame or image that is collected in block 124. As illustrated in FIG. 4, a physiological measurement, such as an EKG measurement of the patient 14, can include a selected amplitude or peak that is measured at each time point $t_1$ through $t_n$ as illustrated in the middle column 4m. An image in the cine loop can also be collected at each of the time points $t_1$ through $t_n$ as illustrated in the right column 4r. As illustrated by arrows $4a_1$, a correlation to the amplitude in column 4m at time point $t_1$ and the image at time point $t_1$ can be made while acquiring images or at any selected point thereafter, similar to that discussed above. For example, the physiology of the patient 14 can be measured beginning at time 0 and the image data can be acquired at time 0 and moving through the time period the physiological measurements can continue as can the acquisition of image frames. Accordingly, the correlation of the image frames to the physiology measurements can be made at any selected time either during or after the acquisition of both the image data and the physiological measurements.

It is understood that the acquisition of the image data and the simultaneous measurement of the physiological data of the patient in block 124 can be collected before or after a simultaneous measurement of the same physiological data of the patient 14 and the tracking of a location of the DRF 48 in block 122. Nevertheless, after both the image data is collected along with a selected physiological measurement and the tracked measurement of the DRF 48 is made along with the collection of the same physiologic data, a correlation of the cine loop frames and the location of the DRF 48 can be made in block 126. As illustrated in FIG. 4, in the left hand column 4l, the tracked location of the DRF 48 for each of the time points $t_1$ though $t_n$ is illustrated. These locations can be correlated to the measured physiological data at time points $t_1$ though $t_n$ as illustrated by the arrows $4a_2$. As discussed above, arrows $4a_1$ show correlation of the physiological measurement and the flows of the cine loop at the various time points. Due to the correlation of the tracked location of the DRF 48 to the physiological data and the physiological data to the cine loop image frames, the tracked location of the DRF 48 can be correlated to each of the frames of the cine loop image data as illustrated by the connecting arrow 130 in FIG. 4.

Thus, individual tracked locations of the DRF 48 can be directly correlated to individual images in the acquired cine loop image data as illustrated in FIG. 4. The correlated cine loop images in block 116 can include correlated images with a tracked location of the DRF 48 that were acquired prior to positioning the DRF 48 within the patient 14. Although the DRF 48 can be positioned within the patient 14 subsequent to acquisition of the cine loop image data, the position of the DRF 48 will be correlated to the various frames in the cine loop image data based upon a correlating data set, such as the measured physiological data in column 4m of FIG. 4.

Regardless of the method of correlation, including those discussed above, each frame or a selected plurality of the image frames from the acquired cine loop, regardless of the source of the images, can be correlated to a selected or tracked location of the DRF 48. The correlation can be direct (e.g. based on tracking the DRF 48 while acquiring the image data) or indirect (e.g. based on using an intermediate measurement, such as a physiological measurement). As illustrated in FIGS. 3 and 4, the location of the DRF 48 at time $t_1$ is correlated to an image that relates to the same time $t_1$. As discussed further herein, a later tracked location of the DRF 48 in block 140 can be used to select which of the images for display or analysis. In other words, it is not required to select, display, or analysis the images 3R, 4R, in the order as acquired, but can be selected based on the instantaneous and delayed determined position of the DRF 48 in any order based on the determined position of the DRF 48.

Once the correlated cine loop image data is related to the respective tracked location of the DRF 48 is made in block 116, the DRF 48 can be further tracked in block 140. As discussed above, the tracking system 30 can track the location of the DRF 48 within the patient 14, such as within the heart 15. The location of the DRF 48 within the heart 15 can be determined to determine the motion or position of the related structure to which the DRF 48 is attached, within the heart 15. As discussed above, the DRF 48 can be positioned at the right ventricle apex and the DRF 48 can therefore determine the position of the right ventricle apex over time as the location of the DRF 48 is tracked. Once the DRF 48 is being tracked within the patient 14, and the correlation of the DRF 48 locations with frames in the cine loop image data has been made in block 116, a recall and or display of a selected frame from the cine loop image data can be made based on the tracked location of the DRF 48 in block 142.

Returning reference to FIGS. 3 and 4, a tracked location of the DRF 48 has been correlated to each image in the cine loop image data. Accordingly, the location of the DRF 48, including x, y, z coordinates and any orientation coordinate relating to, for example, time point $t_3$, are tracked with a tracking system 30 then the image that relates to time point $t_3$ can be displayed on the display device 66. Similarly, as illustrated in FIG. 4, a measured physiology of the patient can be used to select the image from the cine loop image that relates to the time period, such as time point $t_3$ that relates to the image at time point $t_3$. Accordingly, as illustrated in FIGS. 3 and 4, a tracked location of the DRF 48 in block 142 can be used to select an image that correlates to the tracked location of the DRF 48 from the stored data in block 116. The correlated image can then be displayed on the display 66 based upon the tracked location of the DRF 48.

It will be understood that the tracked location of the DRF 48 changes over time due to motion of the patient 14, including motion of the heart 15. The sampling rate of the location of DRF 48 can be any appropriate sampling rate, such as one that correlates to a speed at which the frames in the cine loop were collected. Accordingly, if the images in the cine loop were collected at 30 frames per second, then the position of the DRF 48 can be sampled at about 30 times per second. Each time the position of the DRF 48 is sampled a determination of the position of the DRF 48 can be made and a determination of which the time point $t_1$-$t_n$ the tracked location from block 140 can be determined. A further determination can be made as to which of the images relates to the tracked location of the DRF 48 at the determined time point and that frame can be displayed on the screen at substantially the same sampling rate as the DRF 48. Accordingly, as the DRF 48 moves within the heart 15, the image 64 on the display device 66 can be matched at substantially the same rate. This can allow the image 64 on the display device 66 to substantially mimic a cine loop of the motion of the heart 15. This will illustrate a more realistic and non-static position of the heart 15 over time. It will be understood that the display can be refreshed at any appropriate rate, such as less than 30 frames or more than 30 frames per second, based on a selection of the user 54 or any appropriate selection and/or the frame rate of the acquisition of image frames of the cine loop.

Figure 5:
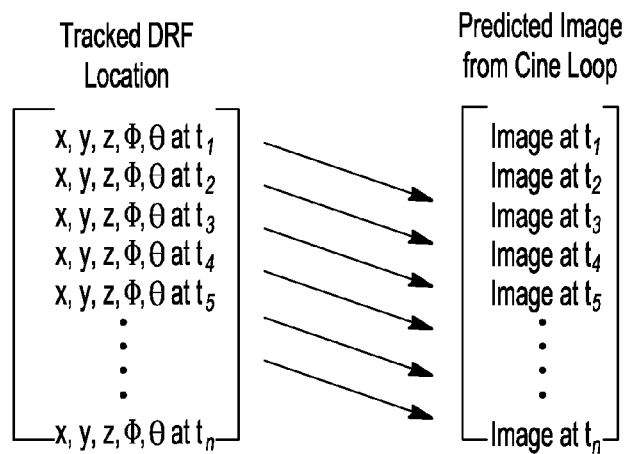
FIG. 5 is a diagram illustrating a predictive correlation between a determined location of a reference tracking device and a cine loop image frame.

Additionally, it will be understood, that various processing and detection, delays may be present. Accordingly, as illustrated in FIG. 5, a predictive image can be selected. For example, if the navigation system 10 determines that the DRF 48 is tracked in block 140 at the location of time point $t_1$ then the image at time point $t_3$ can be selected for display in block 142. The predictive time period can be any appropriate time period such as one to five or one to ten subsequent time point images later relative to the determined location of the DRF 48. The time delay can be any appropriate delay, such as about 1 to 10 seconds, and including about 1-5 seconds, and for example including about 3 seconds. Thus, the tracked location of the DRF in block 140 that relates to time period $t_1$ can be used to predict that the image to be displayed in block 142 can be one that is about 3 seconds later rather than the image that directly correlates to the determined actual tracked location of the DRF 48. Thus, a one to one correlation, that being the time point $t_1$ tracked location of the DRF and a display of the image for time point $t_1$ is not required for display on the display 66.

Figure 6:
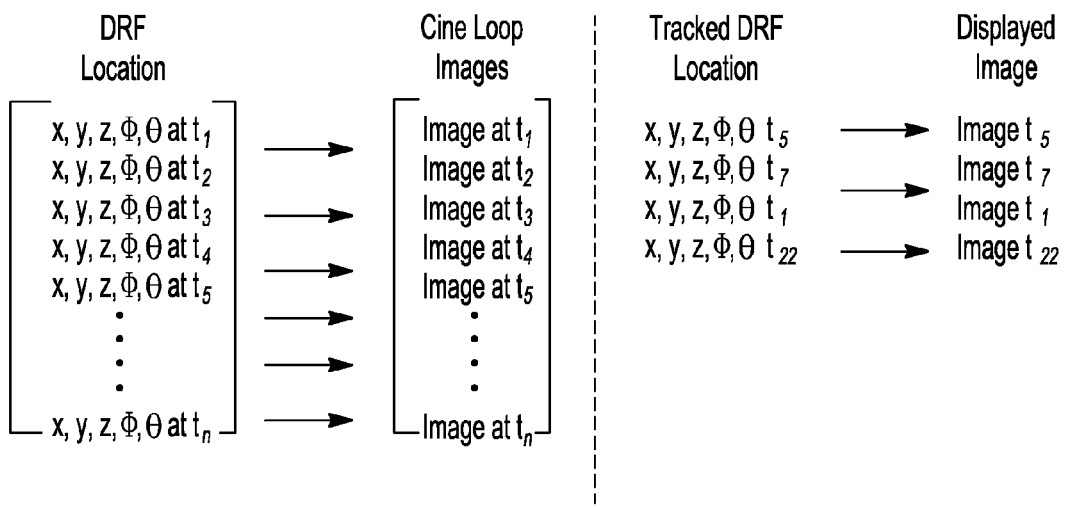
FIG. 6 is a diagram illustrating a sequential correlation between a determined location of a reference tracking device and a cine loop image frame and a further tracking and non-sequential selection of images from the cine loop image frames.

As a further example and explanation, images may also be selected or recalled, in block 142, out of sequence from the acquisition sequence. As illustrated in FIG. 6, a cine loop or plurality of images can be acquired in a selected order Image $t_1$, image $t_2$, to image $t_n$. Each of the images image $t_1$ to image tn can be correlated to a specific tracked locations x, y, z, $\phi$, $\theta$ $t_1$ to x, y, z, $\phi$, $\theta$ $t_n$ of the DRF 48. While tracking the DRF 48 in block 140, the location of the DRF 48 may not move in the same sequence as when the cine loop was acquired. As discussed above, for example, the heart 15 of the patient 14 may not beat in a normal or average sinus rhythm due to the procedure of other trauma to the patient 14. Thus, the locations x, y, z, $\phi$, $\theta$ of the DRF 48 may be out of order of the acquired cine loop of images. Nevertheless, because each image t1 to image tn is correlated to a specific DRF location (e.g. by appropriate methods as discussed above), when one DRF location x, y, z,$\phi$, $\theta$ is determined the image to which it relates can be selected for display or analysis.

As illustrated in FIG. 6, the tracked location of the DRF can include, in tracked locations x, y, z,$\phi$, $\theta$ $t_5$, x, y, z, $\phi$, $\theta$ $t_7$, x, y, z, $\phi$, $\theta$ $t_1$, and x, y, z, $\phi$, $\theta$ $t_{22}$ in that order. The image that relates to each of these specific tracked locations can be displayed in the order as tracked, or as selected, including image $t_5$, image $t_7$, image $t_1$, and image $t_{22}$. Thus, tracking the DRF 48 in block 140 does not simply synchronize the display of the image data, but actually allows for a specific determination and selection of an image for display. It is further understood, that interpolation and "guessing" or averaging algorithms can be used even if the DRF 48 is not tracked at a location identical to a location determined for the correlation.

This allows for exceptional accuracy and true display of the position of a moving structure, such as the heart 15, which will not be altered based on a change in physiology of the patient 14. Also, the physiology of the patient 14 need not be tracked or monitored to determine which image to select for display. Rather, the tracked location of the DRF 48 alone can be used for the selection.

A decision of whether a procedure is to be performed may be made in decision block 150. If no procedure is to be performed then a NO path 148 can be followed to end the method in block 154. However, if it is determined to perform a procedure then a YES path 158 can be followed to track a location of the instrument 80 in block 160. The location of the instrument 80 can be based upon a tracked location of the tracking device 52 that is connected with the instrument 80. The tracked location of the instrument 80 with the tracking device 52 can be used to determine the location of the instrument 80 within the heart 15. The location of the instrument 80 can then be displayed as an icon 166 representing the location of the tracked instrument 80 in block 162. As illustrated in FIG. 1, the icon 166 can be displayed on the display device 68 relative to the image 64 of the heart 15. The image of the heart 64 can be the selected frame from the cine loop in block 142 based upon the tracked location of the DRF 48 from block 140. Thus, the display of the icon 166 representing the location of the tracked location of the instrument in block 162 can relate to a substantially instantaneous and natural and accurate location of the instrument 80 within the heart 15. This is in the alternative to illustrating a single image of the heart 15 as the image 64 which make it appear that the heart 15 is static and motionless and where the instrument 80 may not be in the exact illustrated location due to the movement of the heart 15. The imprecise location illustration of the instrument 80 may be due to the fact that the heart 15 may differ in location from a static image of the heart that is displayed on the display device 66 due to motion of the heart 15.

By allowing the DRF 48 to be tracked in block 140 and to select an image based upon the tracked location of the DRF 48 in block 142, the image on the display device 66 can change over time and be based upon a substantially mechanically tracked location of the heart 15. The DRF 48 can be connected directly to or substantially near a selected portion of the heart 15, a physical location of the heart 15 is tracked with the DRF 48. This can allow for a substantially precise and appropriate selection of the image in block 142 for display on the display device 66.

The heart 15 may undergo changes due to the procedure that is occurring, but the physical location of the heart 15 can be tracked with a tracking device 48 connected to the heart 15. Accordingly, even assuming that the heart 15 of the patient 14 may have a rhythm that is interrupted due to the procedure that is occurring on the patient 14, such as due to the positioning of the instrument 80 within the patient, the physical location of the heart 15 that is tracked with the DRF 48 can be used to select an image of the cine loop to be displayed on the display device 66. Accordingly, an appropriate image can be selected for display on the display device 66 that is unaffected by change in the physiology of the patient 14 due to the procedure and is based substantially or mostly on a physical location of the portion of the patient, such as the heart 15, on which the procedure is occurring.

Accordingly, acquisition of the cine loop image frames and/or the determination of the location of the DRF need not be gated to the patient 14. For example, the determination of the location of the instrument 80 in the patient 14 can be tracked over time and illustrated relative to an image frame of the cine loop that can change over time due to the selection based on the tracked location of the DRF 48. A static image is not necessary or only a limited time of location determination is not necessary as the location of the DRF 48 can be determined at the same time as the location of the instrument 80.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of illustrating a structure, where the structure is in a subject, the method comprising:
   tracking a first plurality of locations or a first plurality of orientations of a reference tracking device during a first period of time, wherein the reference tracking device is fixed to the structure;
   determining a first location or a first orientation of the reference tracking device at a first time point and during the first period of time;
   determining a second location or a second orientation of the reference tracking device at a second time point and during the first period of time;
   acquiring a cine loop of image frames of the structure in the subject during a second period of time, wherein the second period of time is subsequent to the first period of time wherein a first image frame is acquired at a third time point during the second period of time, and wherein a second image frame is acquired at a fourth time point during the second period of time;
   correlating the first image frame to the first location of the first orientation;
   correlating the second image frame to the second location or the second orientation;
   tracking a second plurality of locations or a second plurality of orientations of the reference tracking device during a third period of time, wherein the third period of time is subsequent to the first period of time and the second period of time;
   during the third period of time and based on one of the second plurality of locations or the second plurality of orientations, selecting for display the first image frame or the second image frame;
   tracking a location of an instrument relative to the structure; and
   displaying (i) the selected first image frame or the second image frame, . . . and (ii) an icon representing the location of the instrument relative to the structure and superimposed on the displayed first image frame or the displayed second image frame.

2. The method of claim 1, further comprising:
   generating a correlated image data set based on the correlated first image frame and the correlated second image frame;
   saving the correlated image data set in a memory device; and
   recalling from the memory device the correlated first image frame or the correlated second image frame.

3. The method of claim 1, wherein:
   the correlated first image frame illustrates the structure in the first location and the first orientation; and
   the correlated second image frame illustrates the structure in the second location and the second orientation.

4. The method of claim 3, further comprising:
   measuring a physiological feature of the subject during the first period of time and during the second period of time;
   correlating the correlated first image frame to a first measurement of the physiological feature at the first time point;
   correlating the correlated second image frame to a second measurement of the physiological feature at the second time point;

correlating the first location to a third measurement of the physiological feature at the third time point; and correlating the second location to a fourth measurement of the physiological feature at the fourth time point, wherein the correlating of the first location or the first orientation to the correlated first image frame and the correlating of the second location or the second orientation to the correlated second image frame are each performed based on a respective pair of the first measurement, the second measurement, the third measurement, and the fourth measurement to the first and second image frames.

5. The method of claim 4, wherein the measuring of the physiological feature during the first period of time and the measuring of the physiological feature during the second period of time include measuring an electrocardiogram, respiration, or depolarizations in muscle tissue.

6. The method of claim 1, wherein the organ is a heart of the subject;

the structure is a portion of the heart; and the acquiring of the cine loop of image frames includes acquiring an entire cycle of movements of the heart.

7. A system for generating and illustrating a cine loop of image frames of a structure. where the structure is in a subject, the system comprising:

an imaging device configured to acquire the cine loop of image frames of the structure;

a reference tracking device fixed to the structure in the subject, wherein the reference tracking device moves with the structure;

a tracking processor operable to determine a plurality of locations of the reference tracking device;

an instrument tracking device connected to an instrument, wherein the tracking processor is operable to track (i) a location of the instrument tracking device, and (ii) a location of the instrument based on the location of the instrument tracking device, determine a first location of the reference tracking device at a first time point and during a first period of time, and determine a second location of the reference tracking device at a second time point and during the first period of time;

a physiological measuring device configured to, if the reference tracking device is fixed to the structure subsequent to the acquiring of the cine loop of image frames, measure a physiological feature of the subject based on the first location or the second location; and a navigation processor operable to if the reference tracking device is fixed to the structure subsequent to the acquiring of the cine loop of image frames, correlate a first image frame in the cine loop of image frames to the first location based on the measured physiological feature, correlate a second image frame in the cine loop of image frames to the second location based on the measured physiological feature, select for display the first image frame or the second image frame based on a determined location of the reference tracking device during a second period of time, and display, via a display, (i) the selected first image frame or the selected second image frame, and (ii) an icon representing the location of the instrument relative to the structure super-imposed on the displayed first image frame or the displayed second image frame.

8. The system of claim 7, wherein:

the imaging device is operable to acquire a second cine loop of image frames of the structure in the subject during a third period of time;

the third period of time correlates to the second period of time the first image frame is acquired at a third time point; and the second image frame is acquired at a fourth time point.

9. The method of claim 1, further comprising:

correlating the cine loop of image frames to the first plurality of locations or the first plurality of orientations, wherein the correlation of the cine loop of image frames is not based on a measured physiological feature of the subject.

10. The method of claim 7, wherein the navigation processor is configured to, if the reference tracking device is fixed to the structure prior to the acquiring of the cine loop of image frames, correlate the cine loop of image frames to the plurality of locations, wherein the correlation of the cine loop of image frames is not based on a measured physiological feature of the subject.

* * * * *